United States Patent
Lee et al.

(10) Patent No.: US 11,408,805 B2
(45) Date of Patent: Aug. 9, 2022

(54) METHODS AND MATERIALS FOR EXTRACTING CHROMATIN

(71) Applicant: Mayo Foundation for Medical Education and Research, Rochester, MN (US)

(72) Inventors: Jeong Heon Lee, Rochester, MN (US); Tamas Ordog, Rochester, MN (US); Zhiguo Zhang, Fort Lee, NJ (US); Chad R. Clark, Rochester, MN (US); Wenli Zhang, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1014 days.

(21) Appl. No.: 16/074,233

(22) PCT Filed: Jan. 25, 2017

(86) PCT No.: PCT/US2017/014851
§ 371 (c)(1),
(2) Date: Jul. 31, 2018

(87) PCT Pub. No.: WO2017/136198
PCT Pub. Date: Aug. 10, 2017

(65) Prior Publication Data
US 2021/0181077 A1 Jun. 17, 2021

Related U.S. Application Data

(60) Provisional application No. 62/289,776, filed on Feb. 1, 2016.

(51) Int. Cl.
*G01N 1/40* (2006.01)
*C12N 15/10* (2006.01)
*G01N 1/44* (2006.01)

(52) U.S. Cl.
CPC ....... *G01N 1/4022* (2013.01); *C12N 15/1003* (2013.01); *G01N 1/44* (2013.01)

(58) Field of Classification Search
CPC .......... G01N 1/4022; G01N 1/44; G01N 1/30; C12N 15/1003; C12N 15/10
See application file for complete search history.

(56) References Cited

U.S. PATENT DOCUMENTS

2009/0124510 A1* 5/2009 Porschewski ............ C07K 1/36
530/344
2014/0154674 A1 6/2014 Tackett et al.

FOREIGN PATENT DOCUMENTS

WO WO 2005/116256 12/2005

OTHER PUBLICATIONS

Noberini et al., "Pathology tissue-quantitative mass spectrometry analysis to profile histone post-translational modification patterns in patient samples," Mol. Cell. Proteomics, 15(3):866-77, Mar. 2016.
(Continued)

*Primary Examiner* — Jennifer Wecker
*Assistant Examiner* — Oyeleye Alexander Alabi
(74) *Attorney, Agent, or Firm* — Fish & Richardson P.C.

(57) ABSTRACT

This document provides methods and materials involved in extracting chromatin. For example, methods and materials for obtaining chromatin from formalin-fixed, paraffin-embedded (FFPE) tissues are provided.

8 Claims, 4 Drawing Sheets

(56) References Cited

OTHER PUBLICATIONS

Nazarian et al., "Protein profiling of formalin fixed paraffin embedded tissue: Identification of potential biomarkers for pediatric brainstem glioma," Proteomics Clin. Appl., 2(6):915-24, Jun. 2008.

\* cited by examiner

METHODS AND MATERIALS FOR EXTRACTING CHROMATIN

CROSS-REFERENCE TO RELATED APPLICATIONS

This application is a National Stage application under 35 U.S.C. § 371 of International Application No. PCT/US2017/014851, having an International Filing Date of Jan. 25, 2017, which claims priority to U.S. Application Ser. No. 62/289,776, filed on Feb. 1, 2016. This disclosure of the prior application is considered part of (and is incorporated by reference in) the disclosure of this application.

BACKGROUND

1. Technical Field

This document relates to methods and materials involved in extracting chromatin. For example, this document relates to methods and materials for obtaining chromatin from formalin-fixed, paraffin-embedded (FFPE) tissues.

2. Background Information

Chromatin-based epigenetic analyses can play prominent roles in personalized medicine, especially in cancer diagnosis and treatment. Chromatin immunoprecipitation (ChIP) is a chromatin-based tool used to analyze local and global protein/DNA interactions including genomic distribution and localization of transcription factors and cofactors, epigenetic marks such as modifications of histones and DNA, epigenetic "writers" that establish these marks, as well as the "readers" and "erasers" of these marks.

FFPE samples represent the gold standard for archiving pathology samples, and thus FFPE samples are a resource of samples in clinical research. In some cases, chromatin-based epigenetic assays in the clinical settings are limited to fresh or frozen samples, and not applied to FFPE samples due to the lack of a reliable chromatin preparation method.

SUMMARY

This document provides methods and materials involved in extracting chromatin. For example, this document provides methods and materials for obtaining chromatin from FFPE tissues. As described herein, techniques for processing FFPE tissues can be modified to include a tissue-level, cross-link reversal step applied to deparaffinized tissue that partially reverses the heavy cross-links that result from formaldehyde fixation of tissues before paraffin embedding and archival. Chromatin analysis typically involves both fixation with formaldehyde (typically applied after homogenizing the native or frozen tissue) and reversal of the resultant cross-links after chromatin fragmentation and immunoprecipitation. Formaldehyde fixation as used for tissue archival is harsher by nature making the reversal difficult and suboptimal by currently available techniques. This document provides methods that achieve efficient extraction of high-quality chromatin suitable for chromatin-based epigenetic assays without damaging the chromatin. The methods include incubating a deparaffinized FFPE tissue sample (i.e., before chromatin fragmentation) at a temperature of 65° C. or higher for at least 4 hours. In some cases, this can be performed in the presence of a chromatin stabilization buffer provided herein. A chromatin stabilization buffer can include $Mg^{++}$ chelators to inhibit nuclease activity (e.g., EDTA or EGTA), one or more detergents to increase the solubility of chromatin (e.g., sodium deoxycholate, Triton-X 100, or sodium dodecyl sulfate (SDS)), and EtOH to inhibit nuclease and proteinase activity. The cross-link reversal step provided herein can be performed during the tissue rehydration step that is performed after paraffin removal. In some cases, a tissue-level, cross-link reversal step provided herein can be performed during or after one or more of the tissue rehydration steps and before a cell lysis step.

The methods and materials provided herein can allow scientists and clinicians to perform assays (e.g., targeted or genome-wide epigenetic assays such as ChIP, ChIP-PCR, ChIP-seq, nucleosome positioning, and chromatin accessibility) using chromatin obtained from FFPE (e.g., archived FFPE) tissues. In addition, the methods and materials provided herein increase the effectiveness of chromatin preparation from FFPE samples and can achieve chromatin yields up to 90 to 95 percent of the yields typically obtained using conventional techniques from either fresh and frozen tissues. In some cases, the methods and materials provided herein can provide chromatin yields from FFPE tissues that are greater than 90%, while a commercially available kit may only achieve a chromatin yield of about 2 percent from FFPE tissue.

One step in a standard ChIP assay protocol includes a fixation step with 1% formaldehyde for a short time to stabilize protein/DNA and protein-protein interactions during a long and harsh assay process. While FFPE methods may include treatment with formaldehyde, it is often applied at a higher concentration and for a longer time to ensure proper preservation of the relatively large pieces of tissue samples for downstream applications such as immunohistochemistry. In these cases, FFPE samples may be heavily over-fixed (e.g., more heavily cross-linked), which can make it challenging to obtain chromatin with high yield for ChIP or other chromatin-based epigenetic assays. Over-fixation in FFPE samples can interfere with chromatin analysis in several different ways. First, over-fixation involves the use of harsher chromatin fragmentation methods which, in turn, damages the chromatin. Harsher chromatin isolation approaches may yield marginally more chromatin, but these small gains are usually cancelled out by loss of chromatin integrity. In some cases, over-fixation may manifest in random crosslinking of chromatins with other cellular components resulting in a low signal-to-noise ratio and very lower chromatin yields. The methods and materials provided herein can be used to obtain high quality chromatin without exposing the sample to harsh treatment.

In general, one aspect of this document features a method for obtaining chromatin from a FFPE tissue sample. The method comprises, or consists essentially of, heating tissue material from the FFPE tissue sample to from about 60° C. to about 80° C. for from about 4 hours to about 18 hours, wherein the heating is performed during or after a rehydration step to rehydrate tissue material from the FFPE tissue and before a cell lysis step to lyse cells of the tissue material. The tissue material can be heated to from about 60° C. to about 70° C. The tissue material can be heated to about 65° C. The tissue material can be heated for about 4 to about 12 hours. The heating can be performed during the rehydration step. The tissue material can be heated in the presence of ethanol. The tissue material can be heated in the presence of about 20% ethanol.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
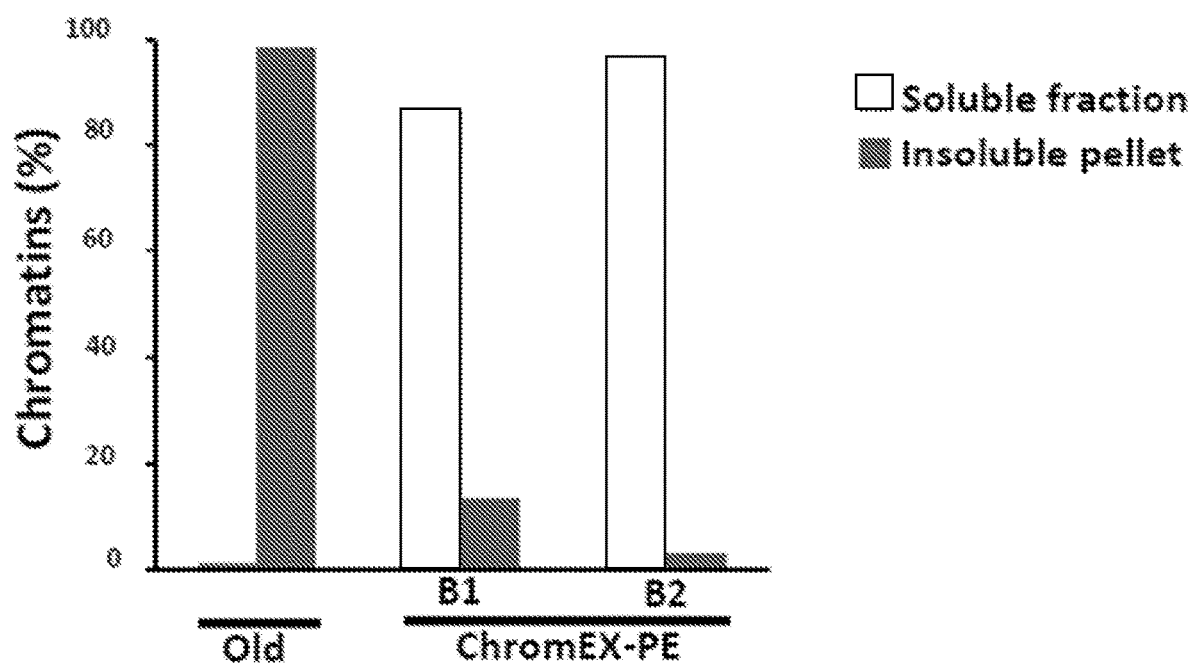
FIG. 1 is a graph plotting the percentage of chromatin present in the soluble fraction and the insoluble pellet following chromatin extraction from FFPE tissue using a chromatin extraction method performed as described elsewhere (World Wide Web at "activemotif.com/documents/1878.pdf"; "Old"), using a chromatin extraction method that includes a tissue-level cross-link reversal step as described in Example 1 and a chromatin stabilization B1 buffer ("B1"), and using a chromatin extraction method that includes a tissue cross-link reversal step as described in Example 1 and a chromatin stabilization B2 buffer ("B2"). The solubilized chromatin is usable for downstream epigenetic assays. This method can be referred to as "ChromEX-PE". Five 20-μm sections of mouse liver FFPE tissues were subjected to chromatin preparation. DNA was isolated from the soluble fractions and the insoluble pellet fractions after the preparation, and the chromatin yield was calculated based on DNA amounts in each fraction. The results demonstrate that the use of a tissue-level cross-link reversal in chromatin stabilization buffers dramatically increases soluble chromatin yield from FFPE tissues (e.g., mouse liver FFPE tissues).

This document provides methods and materials involved in extracting chromatin. For example, this document provides methods and materials for obtaining chromatin from FFPE tissues. As described herein, techniques for processing FFPE tissues can be modified to include a tissue-level cross-link reversal step by heating a FFPE tissue sample to at least 65° C. for at least 4 hours optionally in the presence of a chromatin stabilization buffer. For example, chromatin can be extracted from a FFPE tissue sample using a method that includes a tissue cross-link reversal step where the sample material is incubated at about 65° C. for from about 4 hours to about 18 hours (or overnight) optionally in a chromatin stabilization buffer.

The tissue cross-link reversal step can be performed during the tissue rehydration step that is performed after paraffin removal. For example, after paraffin is removed from a FFPE tissue sample, the material can be rehydrated by exposing the material to ethanol (e.g., progressively less ethanol over a series of steps such as from about 100% ethanol to about 95% ethanol, to about 70% ethanol, to about 50% ethanol, and to about 20% ethanol). During the rehydration, a chromatin stabilization buffer supplemented with 20% ethanol can be used, and the sample can be exposed to a tissue cross-link reversal step of at least 65° C. for at least 4 hours.

A chromatin stabilization buffer can include one or more $Mg^{++}$ chelators such as EDTA or EGTA, one or more detergents such as sodium deoxycholate, Triton-X 100, or SDS, and EtOH (e.g., about 10 to 30% ethanol, about 15 to 25% ethanol, or about 20% ethanol).

In some cases, a tissue cross-link reversal step provided herein can be performed after one or more of the tissue rehydration steps and before a cell lysis step. For example, a tissue cross-link reversal step can be performed with the sample material being in the absence of ethanol and prior to treating the sample with a cell lysis buffer.

Once a chromatin material is obtained from FFPE tissue, the chromatin material can be used to perform chromatin-based epigenetic assays such as ChIP assays, nucleosome positioning assays, and chromatin accessibility assays.

The invention will be further described in the following examples, which do not limit the scope of the invention described in the claims.

EXAMPLES

Example 1—Chromatin Extraction from FFPE Tissues

This following assay protocol was developed to obtain chromatin from FFPE tissues.

The first phase of the chromatin extraction process involved removing paraffin and rehydrating the tissue section as follows:

Deparaffinization, Rehydration, and Tissue-Level, Cross-Link Reversal of FFPE Tissue Sections 1. From one to five FFPE tissue sections (20 μm in thickness) were collected into each 1.5-mL tube.
2. Deparaffinization was started by applying 1 mL of Xylene Substitute solution and incubating the tubes for 10 minutes at room temperature.
3. The tubes were centrifuged at 21,130×g for 3 minutes at room temperature.
4. The supernatant was carefully discarded, and steps 2-4 were repeated four more times for a total of five times. Care was taken to make sure that tiny tissue fragments were not discarded with the supernatant. The centrifugation step was repeated if needed.
5. The deparaffinized tissue was re-suspended in 1 mL of absolute (100%) ethanol.
6. The tubes were incubated for 10 minutes at room temperature.
7. The tubes were centrifuged at 21,130×g for 5 minutes at room temperature. The supernatant was carefully discarded.
8. The pellet was re-suspended in 1 mL of 95% EtOH, and steps 6-7 were repeated.
9. The pellet was re-suspended in 1 mL of 70% EtOH, and steps 6-7 were repeated.
10. The pellet was re-suspended in 1 mL of 50% EtOH, and steps 6-7 were repeated.
11. 0.5 mL of either a B1 buffer or a B2 buffer was added to the tubes, and the tubes were vortexed briefly. The B1 buffer included 10 mM Tris-HCl (pH 7.5), 10 mM NaCl, 10 mM EDTA, 0.5% Triton X-100, 0.1% sodium deoxycholate, 20% EtOH, and a proteinase inhibitor cocktail. The B2 buffer included 10 mM Tris-HCl (pH 7.5), 10 mM NaCl, 10 mM EDTA, 0.5% Triton X-100, 0.1% sodium deoxycholate, 0.1% SDS, 20% EtOH, and a proteinase inhibitor cocktail. The proteinase inhibitor cocktail was obtained from Sigma (Catalog No. P8340, St. Louis, Mo.).
12. The tubes were incubated at 65° C. overnight.

The second phase of the chromatin extraction process involved obtaining the chromatin as follows:

Preparation of Chromatin Input

13. The tubes were centrifuged at 21,130×g for 5 minutes, and the supernatant was carefully discarded.
14. 1 mL of cell lysis buffer (10 mM Tris HCl, pH7.5, 10 mM NaCl, and 0.5% IGEPAL) was added to each tube, and the tubes were mixed well and incubated on ice for 10 minutes.
15. The tubes were centrifuged at 21,130×g for 5 minutes, and the supernatant was carefully removed.
16. 1 mL of cell lysis buffer (10 mM Tris HCl, pH7.5, 10 mM NaCl, and 0.5% IGEPAL) was added to each tube, and the tubes were mixed well and incubated on ice for 10 minutes.
17. The tubes were centrifuged at 21,130×g for 5 minutes, and the supernatant was carefully removed.
18. 2 μL of the lysated sample was diluted in 100 μL of distilled water, and the absorbance was measure spectrophotometrically at 260 nm ($A_{260}$).
19. 1 mL of MNase digestion buffer (20 mM Tris-HCl, pH7.5, 15 mM NaCl, 60 mM KCl, and 1 mM $CaCl_2$) was added to each tube, and the tubes were mixed well.
20. The lysated sample was transfer to 1.5 mL sonication tubes, where were centrifuged at 21,130×g for 5 minutes. The supernatant was carefully removed.
21. 0.25 mL of MNase digestion buffer (20 mM Tris-HCl, pH7.5, 15 mM NaCl, 60 mM KCl, and 1 mM $CaCl_2$) containing a protease inhibitor cocktail was added, and the lysates were resuspended by pipetting.
22. 1-2 μL of 20× diluted MNase was added to each tube, and the tubes were incubated in a thermal mixer (37° C., 1000 rpm×20 minutes). The amount of MNase added per tube was determined based on step 18 as follows: 0.01 U of MNase per 10 μg of chromatin sample quantified according to $A_{260}$ in the step 18.
23. 250 μL of 2×ChIP Stop/sonication buffer (100 mM Tris-HCl, pH8.1, 20 mM EDTA, 200 mM NaCl, 2% Triton X-100, and 0.2% Sodium deoxycholate) was added to each tube.
24. The tubes were sonicated in a Diagenode Bioruptor (15 cycles in Stop/ChIP buffer: 30 seconds on, and 30 seconds off).
25. The tubes were centrifuged (21,130×g, 10 minutes at 4° C.), and the supernatant was collected and placed into a new set of tubes.
26. 250 μL of 1×FFPE Stop buffer 1 (50 mM Tris-HCl, pH8.1, 10 mM EDTA, 100 mM NaCl, 1% Triton X-100, 0.1% Sodium deoxycholate, and 0.05% SDS) was added to the pellets, which were mixed by brief vortex.
27. The tubes were sonicated in the Diagenode Bioruptor (15 cycles in Stop/ChIP buffer: 30 seconds on, and 30 seconds off).
28. The tubes were centrifuged (21,130×g, 10 minutes at 4° C.), and the supernatant was collected and placed into the new set of tubes of step 25.
29. 250 μL of 1×FFPE Stop buffer 2 (50 mM Tris-HCl, pH8.1, 10 mM EDTA, 100 mM NaCl, 1% Triton X-100, 0.1% Sodium deoxycholate, and 0.1% SDS) was added to the pellets, which were re-suspended.
30. The tubes were sonicated in the Diagenode Bioruptor (15 cycles in Stop/ChIP buffer: 30 seconds on, and 30 seconds off).
31. The tubes were centrifuged (21,130×g, 10 minutes at 4° C.), and the supernatant was collected and placed into the new set of tubes of step 25. These tubes contained chromatin input material ready for epigenetic assays.

Example 2—Use of Chromatin Extracted from FFPE Tissues

This following assay protocol is performed to carry out a ChIP assay.

1. IgG or an antibody of interest (about 2 μg) is added to chromatin input materials obtained according to Example 1, and the tubes are rocked at 4° C. overnight.
2. 30 μL of pre-washed protein G-agarose beads (washed twice with 1 mL 1×ChIP buffer) are added to each tube.

3. The tubes are rocked at 4° C. for 3 hours.

4. The tubes are centrifuged at 4,600×g for 1 minute, and the supernatant is removed.

5. The beads are washed with each of the following as separate washes: 1 mL of 1×ChIP buffer, 1 mL of 1×ChIP buffer (5 minute wash on rocker), 1 mL of high salt buffer (ChIP buffer+0.5 M NaCl), 1 mL of high salt buffer (ChIP buffer+0.5 M NaCl) (5 minute wash on rocker), 1 mL of Tris/LiCl buffer, 1 mL of Tris/LiCl buffer (5 minute wash on rocker), and 1 mL of TE buffer twice.

6. 50 µL of 1× elution buffer is added to the beads, and they are incubated at 65° C. for 15 minutes (vortexing 5 seconds for every 3 minutes). An isotherm mixer (Fisher Scientific, Cat. No. 270600F; 65° C., 15 minutes at 1200 rpm shaking) can be used for elution. The elution can be repeated with 50 µL of 1× elution buffer to increase the recovery of yield, and the eluents combined.

Example 3—Use of the DNAs after ChIP Using Chromatin Extracted from FFPE Tissues This following assay protocol is performed to carry out real-time PCR and library preparation for next-generation sequencing.

1. The chromatin eluents obtained according to Example 2 are incubated at 65° C. overnight to reverse cross-link the material. At this point, 1% input of the chromatin input material in the ChIP elution buffer is included.

2. The tubes are briefly centrifuged, and 2 µL of DNase-free RNase A (10 mg/mL, Thermo Scientific Cat. #EN0531) is added to each tube. The tubes are vortexed briefly and incubated at 37° C. for 1 hour.

3. The tubes are briefly centrifuged, and 10 µL of Proteinase K (20 mg/mL, Ambion, Cat. #: AM2546) is added. The tubes are vortexed briefly and incubated at 37° C. for 2 hours.

4. The tubes are briefly centrifuged, and 500 µL of PB buffer (from the Quiagen PCR purification kit or MinElute PCR purification kit) is added. The tubes are mixed very well.

5. The mixture is loaded onto a MinElute column (if DNA concentration is very low) or a PCR purification column, and centrifuged at 7600×g for 1 minute.

6. The pass through is removed, and 650 µL of wash buffer is added. The tube is centrifuged (7600×g, 1 minute).

7. The pass through is removed, and the tube is centrifuged at maximum speed for 1 minute.

8. The column is transferred to a new tube, and 10-20 µL (MinElute) or 50 µL (PCR purification kit) of column elution buffer is added to the center of the column.

9. The tube is centrifuged (21,130×g, 1 minute). The purified DNA is used for real time PCR or library preparation for next-generation sequencing.

Example 4—Buffers

Chromatin Stabilization Buffer B1
10 mM Tris-HCl, pH7.5
10 mM NaCl
10 mM EDTA
0.5% Triton X-100
0.1% Sodium deoxycholate
20% EtOH
Proteinase inhibitor cocktail obtained from Sigma (St. Louis, Mo.; catalog number P8340). The cocktail was described as including AEBSF at 104 mM, Aprotinin at 80 µM, Bestatin at 4 mM, E-64 at 1.4 mM, Leupeptin at 2 mM, and Pepstatin A at 1.5 mM. Each component has specific inhibitory properties. AEBSF and Aprotinin act to inhibit serine proteases, including trypsin, chymotrypsin, and plasmin amongst others. Bestatin inhibits aminpeptidases. E-64 acts against cystein proteases. Leupeptin acts against both serine and cystein proteases. Pepstatin A inhibits acid proteases.

Chromatin Stabilization Buffer B2
10 mM Tris-HCl, pH7.5
10 mM NaCl
10 mM EDTA
0.5% Triton X-100
0.1% Sodium deoxycholate
0.1% SDS
20% EtOH
Proteinase inhibitor cocktail obtained from Sigma (St. Louis, Mo.; catalog number P8340)
Cell Lysis Buffer
10 mM Tris HCl, pH7.5
10 mM NaCl
0.5% IGEPAL
MNase Digestion Buffer
20 mM Tris-HCl, pH7.5
15 mM NaCl
60 mM KCl
1 mM $CaCl_2$
2×ChIP Stop/Sonication Buffer
100 mM Tris-HCl, pH8.1
20 mM EDTA
200 mM NaCl
2% Triton X-100
0.2% Sodium deoxycholate
1×FFPE Stop Buffer 1
50 mM Tris-HCl, pH8.1
10 mM EDTA
100 mM NaCl
1% Triton X-100
0.1% Sodium deoxycholate
0.05% SDS
1×FFPE Stop Buffer 2
50 mM Tris-HCl, pH8.1
10 mM EDTA
100 mM NaCl
1% Triton X-100
0.1% Sodium deoxycholate
0.1% SDS
High Salt Buffer (1× Stop/ChIP Buffer+0.5 M NaCl)
1 ml of 1× Stop/sonication buffer+72 µL of 5M NaCl
Tris/LiCl Buffer
10 mM Tris-HCl, pH8.0,
0.25 M LiCl2
0.5% NP-40
0.5% Sodium deoxycholate
1 mM EDTA
2×TE Buffer: Dilute to 1× to Use
100 mM Tris-HCl, pH8.0
20 mM EDTA
ChIP Elution Buffer (1×)
10 mM Tris-HCl, pH8.0
10 mM EDTA
150 mM NaCl
5 mM DTT
1% SDS Example 5—Use of Chromatins Obtained from FFPE Tissue The following was performed to determine chromatin yields from mouse liver FFPE tissues obtained by a conventional ('old') technique and the ChromEX-PE technique. Five 20-μm sections of mouse liver FFPE tissues were subjected to chromatin preparation according to a previously published method ("Old") or ChromEX-PE. Two different chromatin stabilizing buffers (B1 and B2) were tested with ChromEX-PE. DNA was isolated from the soluble fraction and insoluble pellet fraction after the preparation, and the chromatin yield was calculated based on DNA amounts in each fraction. The results demonstrate that ChromEX-PE dramatically increases soluble chromatin yield from mouse liver FFPE tissues (FIG. 1).

Figure 2:
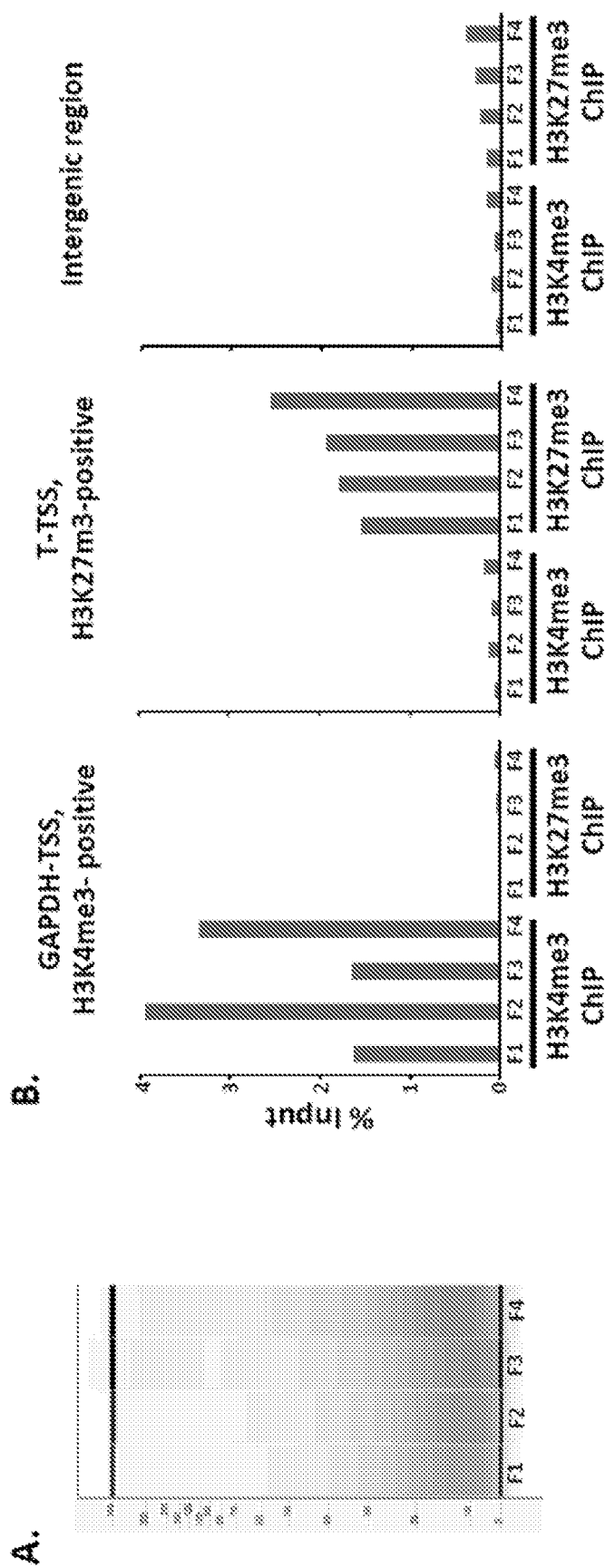
FIG. 2A is an image showing the DNA isolated from the chromatin preparation. Five 20-μm sections of four different mouse liver FFPE tissues (F1, F2, F3, and F4) were subjected to chromatin preparation using ChromEX-PE as described in Example 1. DNA was purified after cross-link reversal of soluble chromatin and analyzed on a Fragment Analyzer (Advanced Analytical Technologies. Inc. (AATI), Ames, Iowa). DNA size markers are shown on the left. The results indicate that the majority of chromatin prepared from FFPE tissues using a chromatin extraction method that includes a tissue cross-link reversal step in the chromatin stabilization buffer B1 as described in Example 1 is suitable for downstream epigenetic assays, including targeted ChIP and ChIP-sequencing (ChIP-seq).
FIG. 2B shows ChIP efficiencies from soluble chromatin by ChIP-qPCR. Input chromatin samples were subjected to ChIP assays targeting H3K4me3 and H3K27me3 histone marks. The ChIP products were analyzed by real-time PCR in a transcriptionally active region (GAPDH-TSS, positive for H3K4me3, but not for H3K27me3), in a developmentally silenced region (T-TSS, positive for H3K27me3, but not for H3K4me3), and in an intergenic region (negative for both H3K4me3 and H3K27me3) in the mouse liver. The relative enrichment of the histone marks in the tested loci is shown as the percentage of input (% input). The results demonstrate that the chromatin prepared from FFPE tissues using ChromEX-PE is compatible with targeted ChIP assays.

In another experiment, five 20-μm sections of four different mouse liver FFPE tissues (F1, F2, F3, and F4) were subjected to chromatin preparation by ChromEX-PE. DNA was purified after cross-link reversal of input chromatin and analyzed on an AATI Fragment Analyzer (FIG. 2A). Input chromatin samples were subjected to ChIP assays targeting H3K4me3 and H3K27me3 histone marks. The ChIP products were analyzed by qPCR in open chromatin (GAPDH-TSS, H3K4me3-positve), in a developmentally silenced region (T-TSS, H3K27me3-positve), and an intergenic region in the mouse liver (FIG. 2B). The relative enrichment in the tested loci was shown as the percentage of input (% input). These results demonstrate that the chromatin prepared by ChromEX-PE from FFPE tissues is compatible with targeted ChIP assays.

Figure 3:
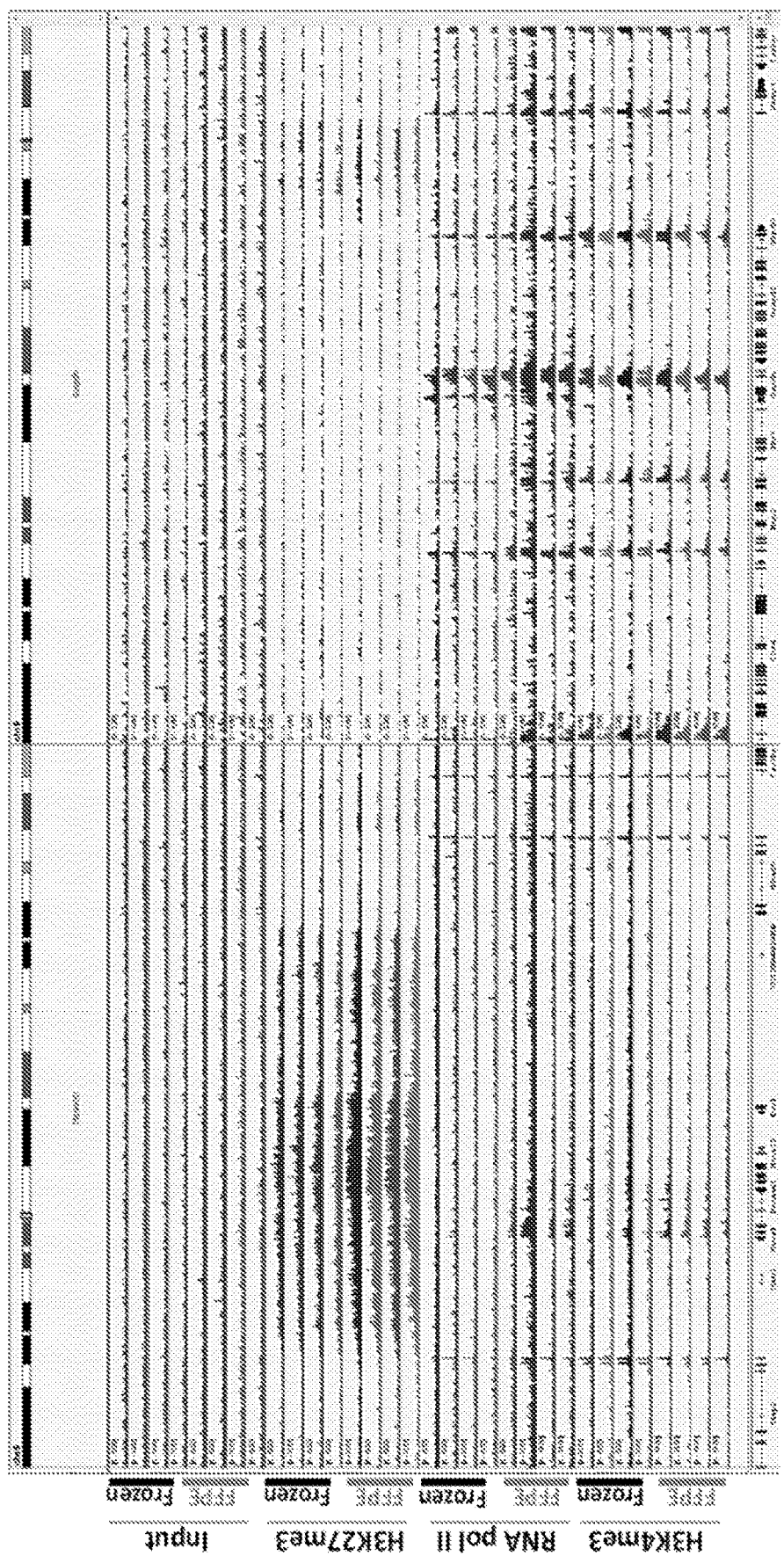
FIG. 3 shows ChIP-sequencing results in FFPE-derived chromatin demonstrating the feasibility of obtaining high quality chromatin following cross-link reversal as described herein. Five 20-μm sections of four different mouse liver FFPE tissues were subjected to chromatin preparation using a chromatin extraction method that includes a tissue cross-link reversal in the chromatin stabilization buffer B1 as described in Example 1. The chromatin was subjected to ChIP for histone marks H3K4me3, H3K27me3, and RNA polymerase II. Next-generation sequencing libraries were prepared from ChIP and input DNAs and sequenced on Illumina HiSeq2000 platform. The sequence reads were mapped to the mouse reference genome and visualized by the IGV browser (Broad Institute, Cambridge, Mass.). Frozen tissues from the same mouse liver tissues were processed for ChIP-seq as references. The results demonstrate that the chromatin prepared from FFPE tissues using a chromatin extraction method that includes a tissue cross-link reversal in the chromatin stabilization buffer B1 as described in Example 1 is compatible with ChIP-seq, and the results are comparable to the results obtained in frozen samples using conventional techniques.

In another experiment, five 20-μm sections of four different mouse liver FFPE tissues were subjected to chromatin preparation by ChromEX-PE. The chromatin was subjected to ChIP for histone marks H3K4me3 and H3K27me3 and RNA polymerase II. The next-generation sequencing libraries were prepared from ChIP and input DNAs and sequenced on Illumina HiSeq2000 platform. The sequence reads were mapped to the mouse reference genome and visualized by the IGV browser (FIG. 3). Frozen tissues from the same mice were processed for ChIP-seq as references. The results demonstrate that chromatin prepared by ChromEX-PE from FFPE tissues are compatible with ChIP-seq.

Example 6—Preparing a Chromatin Preparation from FFPE Tissue

Figure 4:
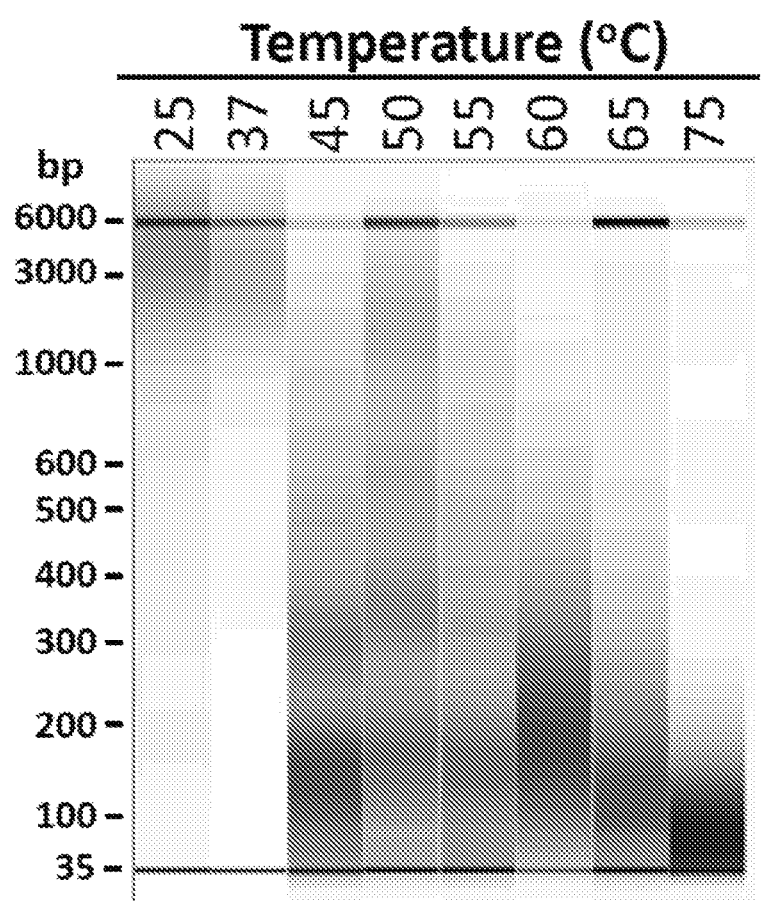
FIG. 4 is an image showing DNA isolated from chromatin. Mouse liver FFPE tissues were subjected to chromatin preparation at the indicated temperatures using ChromEX-PE as described in Example 6. DNA was purified after cross-link reversal of soluble chromatin and analyzed on an AATI fragment analyzer (Ames, Iowa). The results indicate that the majority of chromatin prepared from FFPE tissues using a chromatin extraction method that includes a tissue cross-link reversal step in the chromatin stabilization buffer B1 between the temperatures of 25° C. and 75° C. as described in Example 6 is suitable for downstream epigenetic assays, including targeted ChIP and ChIP-sequencing (ChIP-seq).

FFPE mouse liver tissues were deparaffinized and rehydrated up to 20% EtOH. Equal amounts of tissues in the chromatin stabilization buffer (chromatin stabilizing buffer B1) were incubated at different temperatures for tissue-level cross-link reversal and subsequently processed by Chrom-Ex PE. The DNA from isolated chromatin was analyzed by AATI fragment analyzer to evaluate chromatin quality. The results demonstrate that Chrom-Ex PE in the temperature range of 45-55° C. generated the nucleosomal digestion pattern that is typically produced from frozen tissues and cell lines (FIG. 4). This observation suggests that Chrom-Ex PE performed within the 45-55° C. temperature range can be used as a method of chromatin preparation from FFPE tissues for chromatin-based epigenomic assays along with ChIP-seq. The Chrom-Ex PE in the temperature range 60-65° C. generated high quality chromatin input of about 100-300 bp of DNA (FIG. 4), which is ideal for ChIP-seq.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for obtaining chromatin from a FFPE tissue sample, wherein said method comprises heating tissue material from said FFPE tissue sample to from about 25° C. to about 75° C. for from about 4 hours to about 18 hours, wherein said heating is performed during or after a rehydration step to rehydrate tissue material from said FFPE tissue and before a cell lysis step to lyse cells of said tissue material.

2. The method of claim 1, wherein said tissue material is heated to from about 60° C. to about 70° C.

3. The method of claim 1, wherein said tissue material is heated to about 65° C.

4. The method of claim 1, wherein said tissue material is heated for about 4 to about 12 hours.

5. The method of claim 1, wherein said heating is performed during said rehydration step.

6. The method of claim 5, wherein said tissue material is heated in the presence of ethanol.

7. The method of claim 5, wherein said tissue material is heated in the presence of about 20% ethanol.

8. The method of claim 1, wherein said tissue material is heated to from about 45° C. to about 55° C.

* * * * *